United States Patent
Gaydos et al.

(10) Patent No.: US 7,762,596 B1
(45) Date of Patent: Jul. 27, 2010

(54) URINE SAMPLE RETRIEVAL DEVICE

(76) Inventors: Kelly M. Gaydos, 807 E. Smithfield St., Greenock, PA (US) 15047; Gwendolyn C. Davis, 7311 Bennett St., Pittsburgh, PA (US) 15208

( * ) Notice: Subject to any disclaimer, the term of this patent is extended or adjusted under 35 U.S.C. 154(b) by 391 days.

(21) Appl. No.: 12/071,643

(22) Filed: Feb. 25, 2008

(51) Int. Cl.
*A01K 29/00* (2006.01)
(52) U.S. Cl. .................... 294/1.5; 119/161; 600/573
(58) Field of Classification Search ............. 294/1.3, 294/1.4, 1.5, 55; 119/161; 15/257.3; 600/573, 600/574; 141/344, 390, 391
See application file for complete search history.

(56) References Cited

U.S. PATENT DOCUMENTS

| | | | | |
|---|---|---|---|---|
| 220,576 | A | * | 10/1879 | Chilis ..................... 141/98 |
| 2,794,457 | A | * | 6/1957 | Nicodemus ............. 141/344 |
| 3,490,501 | A | * | 1/1970 | Lefebvre et al. ......... 141/84 |
| 4,094,020 | A | * | 6/1978 | Franklin ................. 600/574 |
| 7,128,352 | B1 | | 10/2006 | Phippen |
| 7,214,199 | B1 | | 5/2007 | Yastrebov |
| 2005/0177070 | A1 | | 8/2005 | Levinson |
| 2006/0064033 | A1 | | 3/2006 | Stewart et al. |
| 2006/0064034 | A1 | | 3/2006 | Stewart |
| 2008/0077047 | A1 | * | 3/2008 | Karvas et al. ............ 600/574 |

FOREIGN PATENT DOCUMENTS

JP  2001-149265  6/2001
JP  2006-340707  12/2006

* cited by examiner

*Primary Examiner*—Dean J Kramer
(74) *Attorney, Agent, or Firm*—Donald Grant Kelly

(57) ABSTRACT

Device and method for collecting animal urine including a tray mounted to an elongated handle which is at least partially hollow. The handle, at one end, is interconnected to a tray to be deployed beneath the animal in advance of urination. At its other end, the handle is configured as a hand grip. Located at a point along the handle and spaced away from the tray, is a collection bottle mount to which is connected a specimen collection bottle within direct flow connection with the tray via the partially hollow handle. The bottle and mount serve as a second handle for steadying control of the device. By tipping the handle such that the tray is raised above the handle, urine collected in the tray is drained directly to the bottle. The bottle includes a slit wafer ensuring against spillage when the bottle is removed for recapping and transport for analysis.

10 Claims, 4 Drawing Sheets

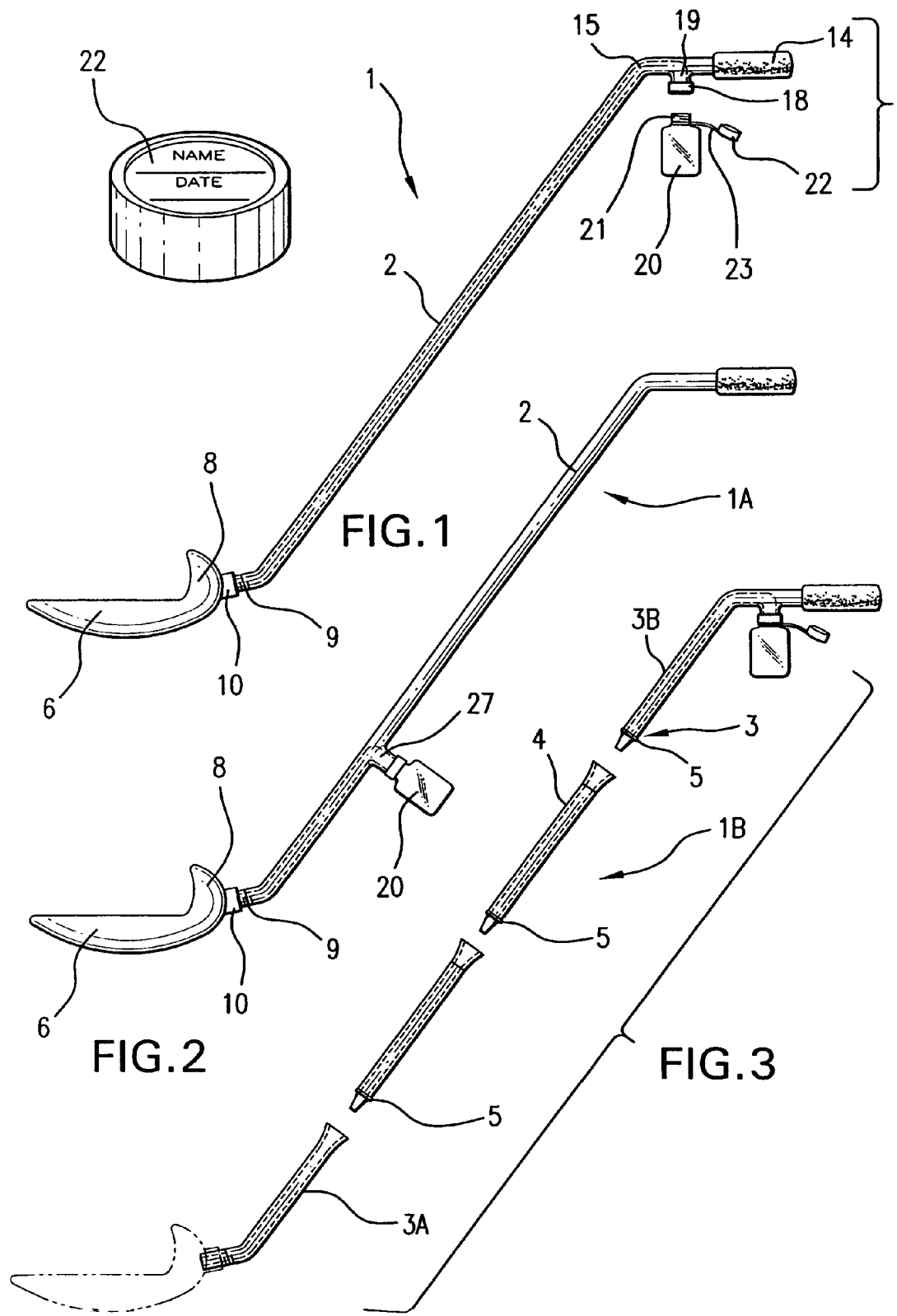

URINE SAMPLE RETRIEVAL DEVICE

CROSS REFERENCE TO RELATED APPLICATIONS

Not applicable

STATEMENT REGARDING FEDERALLY SPONSORED RESEARCH OR DEVELOPMENT

Not applicable.

REFERENCE TO SEQUENCE LISTING

Not applicable.

REFERENCE TO MICROFICHE APPENDIX

Not applicable.

BACKGROUND OF THE INVENTION

This invention generally relates to the field of medical diagnostics where tools or implements are deployed in a urine capturing process for subsequent laboratory analysis. More specifically, the present inventive technology focuses upon devices, systems, kits and their method of use in securing animal urine specimens in the field and storing those specimens for subsequent veterinary testing. The novel invention is particularly suited for capturing urine from domestic pets such as dogs, but may of course have broader application, for example for zoo animals, farm animals and the like.

It is well known, for example, that family pets such as dogs may encounter a number of health issues resulting in a veterinarian's requirement for a urine specimen for laboratory testing. For instance, dogs may develop kidney disease or even chronic kidney failure as a result of nephritis brought on by bacterial invasion. Dogs also may develop diabetes which generally calls for a regular schedule of testing of urine glucose levels. Urine analysis is used for a variety of other pet maladies such as hyperadrenocorticism (also known as Cushing's disease) or leptospirosis. Detection and treatment of such conditions almost always involve testing and regular monitoring of urine samples.

Uncontaminated urine samples, when required, are taken by veterinarians through a technique known as cystocentesis. This procedure involves withdrawal of a urine sample directly from the pet's bladder by means of an inserted needle. Another option is to take a urine sample by means installing a bladder catheter. These techniques may or may not require pet sedation but, in any case, can be relatively expensive for the pet owner. Invasive collection also poses risk of new infections. For these reasons, and when appropriate, a veterinarian may suggest alternative, indirect collections of less "perfect" specimens (e.g., those deposited under field conditions). Field collection methods, though simple and straightforward in concept, pose considerable challenges in execution.

Pet owners (or caretakers) who have been sent home to capture a pets' fresh urine samples and to preserve them for clinical analysis often will turn to the more obvious collection implements such as spoons, cups, saucers and soup ladles. They quickly find this more difficult than expected and their pets less than cooperative. Duck-walking while stalking a pet, grasping a leash in one hand and soup ladle in the other, surely strains the pet owner's back and knees, not to mention the strain on their patience and dignity.

Creative owners have been known to wire or tape small pie pans or margarine tubs to broom handles or yardsticks. Others report regularly restricting their pets' walks to confined pathways across plastic sheets from which puddles are siphoned, drained or soaked into a sponge. With each makeshift innovation, efforts to transfer tediously collected urine pose still greater challenges, the more serious among these being accidental spills on hands and clothes. With some pet ailments such as leptospirosis (mentioned above), urine contact on the pet owner's skin can pose truly serious consequences.

This is a growing national problem, particularly in light of the significantly increased attention and wealth directed toward the healthcare and wellbeing of domestic pets. The arrival of major advances in animal disease detection and treatment technologies is accompanied by significantly increased demands for urine sample collection. Increased demand for specimen collections have brought no significant improvement changes in capture techniques, nor have pet handlers' skills improved. A few inventors have stepped forward with possible solutions, but with only very limited success.

The Yastrebov U.S. Pat. No. 7,214,199 presents a collection tray or catch basin with a funnel at one end of the tray basin. Threadably interconnected at the funnel end tap point is a collection bottle. Once urine is deposited into the basin, the entire device is tilted toward the tap point and funneled directly into the bottle.

Yastrebov's catch basin device can be manually wielded by the pet owner, but the structural configuration requires intimate physical proximity to the urinating pet. Also, Yastrebov's design does nothing to relieve the pet handler's painfully awkward squatting pose. Moreover, as the urinating pet briefly "marks" one spot and moves ahead for further "marking," the squatting handler cannot easily follow. Besides, the likelihood of spooking the pet with the Yastrebov device is obvious, resulting in a wary pet becoming still more noncooperative. Most notably, Yastrebov presents no safeguards against manual contact with the specimen drips from the funnel and bottle as the latter is removed.

U.S. Pat. No. 7,128,352 issued to Phippen illustrates a pet urine collection device having an elongated handle in the form of a rod or wire which is configured to hold a cup or other container in place beneath the pet. A lid is pivoted into place and the cup or container is lifted from the handle. While the Phippen device offers the pet owner the luxury of standing rather than squatting during the urine collection stage, the collection is prone to specimen spillage and handler skin contact due to the container's open condition pending final closure.

Shinpo's published Japanese Patent Document No. JP2006-340707 is physically similar in some respects to the Phippen device (described above) in its depiction of an elongated handle to the distal end of which is mounted an absorbent sheet. However, this is not a specimen collection device. Instead, for environmental reasons, the sheet is interposed between the urinating pet and its "marking" target. Urine collected on or in the sheet would be difficult to extract as a sample and, even if it can be extracted, the specimen certainly would not have the purity required for effective analysis.

Other known urine collection systems were developed for human urine capture, but have features worth noting in the present context. For example, Sumiya's Japanese patent document No. JP2001-149265 presents a urine collecting device including a collection port at its distal end. A hose interconnects the collection port to a container where the urine will be captured. This is intended as a portable toilet configured to be stationary on a base with an upstanding collection area, not a collection device that could be inverted and extended beneath a urinating pet.

Inventors Stewart et al. disclose midstream urine sampling devices in which sample collection containers or vials are attached between proximal and distal ends of their respective devices as depicted in US Published Patent Application No. 2006/0064033 and No. 2006/0064034. Each shows a collection funnel adapted for relative placement about a urine source. A collection chamber is adapted to allow for collection of a midstream portion of a urine discharge. By purposely allowing the initial portion of the urine discharge to escape or bypass a collection chamber, the embodiments of the inventions provide for collection of a more preferred midstream portion of the discharge. Vials for collecting the samples include air relief features at their entryways to facilitate the collection.

In US Published Patent Application No. 2005/0177070, Levinson discloses a urine collection device including an elongated tubular conduit with a funnel-shaped receiver at its proximate end and an open distal end. Between the ends is positioned a detachably mounted collection container. This device of course is for collection at an upper end thereof, followed by urine flow downwardly past a collection container with the excess ejected from a bottom opening. Obviously this structure would not be suited to a urine-collecting pet owner.

Thus, presently existing technology discloses a wide range of urine sample collection systems, devices, methods and kits, some of which are suitable for capturing pet urine while others are limited to human urine sampling. Pet urine specimen collection arrangements range from home remedies such as pans and spoons to commercial hand wielded collection devices. These, as noted above are not without attendant shortcomings in terms of effectiveness and sanitary preferences.

What clearly is missing from the prior art, yet decidedly needed, is a pet urine sample capturing device, system and method which is, at once: (1) capable of managing the urine sample collection procedure from a position remote enough to be unobtrusive and non-threatening to the pet; easily manipulated and guided by a standing or ambulatory pet owner/handler; configured to be easily and steadily stationed beneath the pet during urination; tiltable without spillage to enable clean and efficient transfer of the collected urine directly into a collection bottle configured for subsequent removal without spillage or soiling the owner's clothing or contaminating the hands.

Further needed is a sample collection kit, device and method which feature simple, lightweight materials configured to be assembled and disassembled as needed, and adjustable in length to accommodate shorter or taller users. Ideally, between uses these components can be neatly and unobtrusively stored. The present invention, as will be fully discussed herebelow, provides all of these features and advantages.

BRIEF SUMMARY OF THE INVENTION

The present invention features, inter alia, a urine sample collection device, system, method and kit to be principally applicable to domestic pets such as dogs and cats. Without intention to unduly limit the invention, it is disclosed herein in the context of collection dog urine by a pet handler. As will be evident, the present invention resolves shortcomings of earlier "solutions" and, beyond that, offers a number of additional features.

By way of brief summary, the urine sample collection invention fully described below features a collection tray mounted to an elongated handle, wherein the elongated handle is a rod that is at least partially hollow or tubular. The rod may be substantially straight or provided with at least one curve or bend. Ideally, a gradual bend from the tray and generally upward, followed by another gentle curve rearward toward a grip results in a device that will offer a pet a maximum degree of comfort and ensure that the handler is a maximum distance away from the pet and possible contamination.

The collection tray has a narrowed leading edge separated from its larger, trailing funnel-shaped end by a central catch basin. The handle/rod, at its distal end (that is, the end remote from the pet handler as will be explained), is interconnected at a relatively low point on the tray basin so as to quickly receive a captured specimen from the catch basin, once the rod and tray are lifted with the collection tray tipped toward its funnel end. A splash guard may be mounted as an optional aid in capturing discharge over-shots particularly by male pets.

Along a hollow portion of the rod, remote from the catch basin, a sample or specimen collection container is temporarily fastened so that its interior is in direct flow communication with the hollow portion of the handle rod. As the rod and tray are lifted and tipped, captured urine flows from the basin directly into the hollow portion of the rod and on to the specimen collection container. The terms user or pet handler in this context are terms of convenience referring to the person in charge of the urine sample collection and employing the inventive kit, device and method. This person may be a pet owner, caretaker, veterinarian, or other individual.

To facilitate manipulation and guidance of the tray, the rod, is provided with a primary hand grip at its proximate end (i.e., at the pet handler's location). At its distal end, the rod is interconnected at an obtuse angle relative to the collection tray and has a length (between primary hand grip and tray) sufficient to permit a pet handler to stand substantially upright and at a respectfully remote location behind the pet being "walked."

In this substantially upright position, the pet handler wields the inventive device and gently guides the collection tray beneath the dog. Passage of the collection tray beneath the pet is facilitated by its narrowed leading edge. When necessary, the pet handler may further ensure stealthy and accurate manipulation of the tray by grasping the collection container as a secondary hand grip. Steady manipulation of the device is important when attempting to avoid spooking a nervous pet. Also important is the fact that the present invention facilitates tray manipulation and collection by the handler in a standing position, and at a significant distance so as not to disturb the animal. With relatively little practice, the handler is usually capable of manipulating the device with only one hand, collecting the urine, tilting the handle and transferring the collected urine to the container.

Once a urine sample is captured in the catch basin and the tray is easily tipped toward its heel or funnel end and lifted only to a slightly higher level relative to the rod handle end. This permits the urine to be flow through the rod hollow portion (which may terminate at or immediately beyond the collection container. When the urine sample is within the collection container, the tray is again lowered.

The collection container or bottle is configured to keep the sample from flowing outwardly from the container and returning into the hollow rod handle. If the collected specimen is insufficient, another attempt may be made to capture more urine in the catch basin. When the collection session has ended, the container is removed from its connection tap point and capped for storage pending delivery to the veterinarian. The device may be disassembled for cleaning and stored in a kit box for later use.

The invention will be best understood by reference to the following detailed description of an illustrative embodiment when read in conjunction with the accompanying drawings, wherein:

BRIEF DESCRIPTION OF THE DRAWINGS

FIG. 1 is a side elevation of the urine sample retrieval device of the present invention further including, within its bracket, a disconnected specimen container and a perspective view of the container cap;

FIG. 2 is a side elevation similar to that of FIG. 1, illustrating an alternative location for a specimen container;

FIG. 3 shows a side elevation of an optional handle configuration comprising components which may be disassembled for storage, with a tray portion of the device shown in phantom lines;

DETAILED DESCRIPTION OF THE INVENTION

Figure 4:
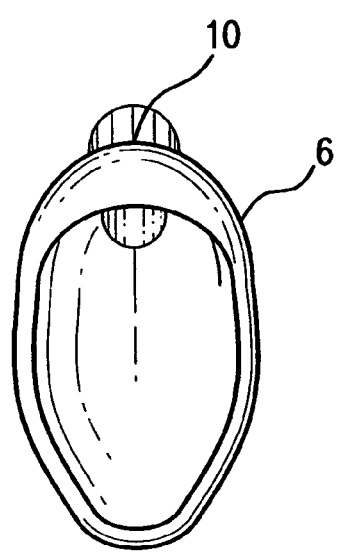
FIG. 4 is a front perspective view of the collection tray and catch basin.
Figure 5:
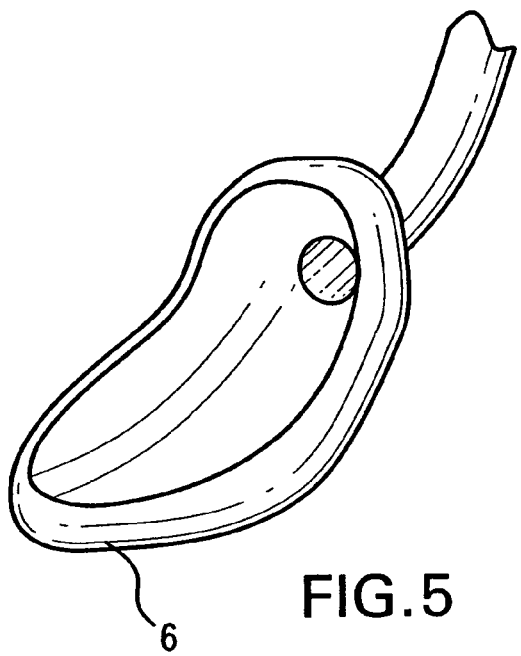
FIG. 5 is a left side perspective view of the collection tray and catch basin shown in FIG. 4.

As viewed in FIG. 1, the embodiment illustrated and described includes a sample collection tray (or catch basin) 6. Tray 6 may have a substantially rounded bottom or substantially flat bottom, understanding that a generally rounded basin will enhance tray capacity and limit spillage, while a flatter bottom affords a lower tray profile. The collection tray as presented in detail in FIGS. 4 and 5 may be relatively narrow at its leading end (i.e., the end to be strategically moved beneath the pet) and configured to expand toward its downstream trailing end or heel to form hood 8. This hood 8 collaborates with the trailing end of tray 6 to define a funnel.

At the trailing end of tray 6, and disposed at a relatively low point thereon, is a drain hole interconnected by connector 10 to a distal end of rod handle 2 which is at least partially hollow, for a purpose to become apparent. The interconnection of handle 2 and connector 10 may be pivotal (as, for example, a universal connection such as a typical showerhead connection) to add flexibility to the device 1. As will be explained in more detail, the pet handler grasps rod handle 2 at its proximal end and extends its distal end outwardly toward the pet location.

Rod handle 2 of device 1 is illustrated (by way of example only, and not intended as limiting the claimed invention) as being substantially straight and having an overall length in the range of about 44". Within reason, rod handle 2 can be of any length to accommodate different (1) pet handler height and/or (2) preferred distance between the pet handler and the pet during use of the device 1. Further, rod 2 need not be substantially straight, but may take other forms within obvious boundaries. For example, from its proximal to distal end, rod 2 may advantageously follow a substantially parabolic path, rising somewhat as it nears the tray. This configuration relatively flattens the interconnection at 10 between tray 6 and rod 2 and facilitates drainage of the specimen into the hollow interior of rod 2. While angles formed in device 1 between tray 6 and handle 14 are show as relatively sharp, gentler curves are just as effective and certainly more aesthetic.

Rod handle 2 is constructed to be of light-weight plastic, fiberglass, thin metal, and the like) and is generally hollow throughout much or most of its length from tray 6 to container mount 19, to be described. The entirety of device 1 is fabricated or constructed from one or more materials that will not react with, or otherwise compromise the chemical purity of the collected urine sample. Such structural materials are well known, particularly in the medical instrumentation and chemical engineering fields. At the remote or distal end 15 of rod handle 2, where it is configured to be held by the user, a suitable handgrip 14 is provided.

As illustrated in FIG. 3 as device 1B, rod handle 2 may be provided as complementary sectional components (3A, 3B, 4 etc. illustrated with leak proof rubber gaskets 5 to stem seepage). Assembled components of rod handle 2 are removably attached to tray 6 by threads 9 at connection 10 so as to facilitate disassembly for storage. Further, adding and/or removing component sections will adjust the length of device 1B to suit the user. Disassembly of the device 1 ensures that a standard work sink will accommodate all components as they are washed, so as to keep device 1 relatively sanitary for its next use.

Rod handle 2 is obtusely angled downwardly from grip 14 toward collection tray 6. At a selected location (discussed below) along the length of rod handle 2, is a "tap point" container-mount 19 configured to accept a specimen collection container 20 placed thereon. By way of example, only, container-mount 19 is illustrated as threaded to accept the complementarily threads 21 of collection container 20.

Container-mount attachments other than screw threads may be employed, such as interlocking tabs and slots, friction-fit or rim-in-groove (where the collection container 20 is "pressed" or "snapped" into place). The tap point container-mount 19 may be at any convenient location along the hollow handle as long as the handler can manage the positioning of the tray without strain or discomfort, and without annoying the pet. A more specific container-mount location does, however, pose significant advantage described as follows.

It is helpful to the handler if she/he is able to reach and grasp the specimen collection container 20 during use. Boundaries of possible container-mount locations are seen comparatively in FIGS. 1 and 2, wherein are illustrated two possible container—mounts 19 and 27. This is because the container-mount 19 or 27 and the respective container 20 afford a handy, secondary hand-grip for pet handler's "other hand" (i.e., the hand not grasping handgrip 14). While the device 1 is designed and configured principally for one-hand use, a two-hand grip may occasionally be helpful.

For example, where a nervous pet is involved, supporting device 1 with two hands affords more precise manipulation in guiding and unobtrusive collection process. A crucial attribute of the present invention is its capacity for deployment without unwelcome contact with the urinating pet. This dual handle feature ensures that advantage. However, it is important to remember that this device 1 may be used in almost all cases as a single-hand urine collection tool. With its relatively lightweight and narrow configuration, as well as generous length, the handler may easily maneuver device 1 into collection position from a respectable distance so as not to disturb the animal.

An element configured to keep a collected urine sample from spilling from collection container 20, particularly upon removal thereof from container-mount 19, and prior to final capping, is presented as another feature of the present invention. This may be an internal lip (not shown) integrally formed within a neck of collection container 20 or a separate element in the form of a membrane wafer 24 disposed immediately within container 20 opening. Such anti-spill feature also acts to prevent collected urine from draining from container 20 back into the hollow rod 2.

Flexible membrane wafer 24 may be installed (as by friction-fit or snap-fit) immediately within the collection container 20 entrance. A feeder tube 28 accessory may be interconnected by container 20 connection threads 30. Feeder tube 28 is pointedly configured to pierce membrane wafer 24 as the container 20 is set into place. The membrane wafer 24 may also have one or more minute through-holes (not shown) permitting air to escape from the container so as to facilitate in-flow of captured urine.

As a further feature, wafer 24 may include pre-formed slits 26 for permitting feeder tube 28 insertion without damaging wafer 24. The pressing, piercing action of feeder tube 28 spreads pre-formed slits 26 to simultaneously permit urine entry and air escape. As the collection container 20 is withdrawn from container-mount 19 and away from feeder tube 28, slits 26 in the flexible wafer 24 are self-sealing. It is important that the lip (not shown) and/or the slit wafer 24 affords escape of air from the bottle as urine is collected therein, and that it serves well in blocking spillage when disconnected from container-mount 19 pending re-capping.

Figure 6:
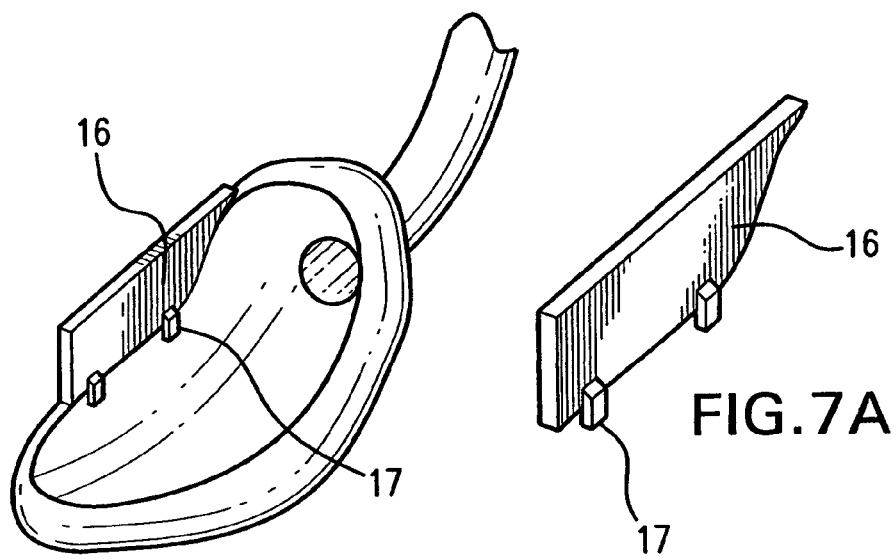
FIG. 6 is a left side perspective view similar to FIG. 5, illustrating an optional splash guard accessory.
Figure 7A:
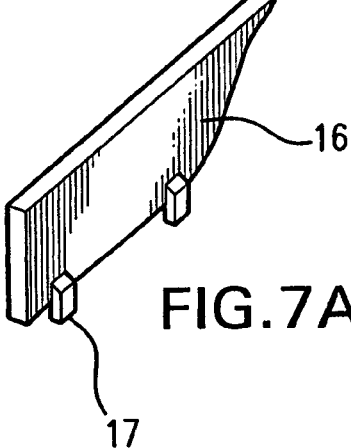
FIG. 7A is a left side perspective of the splash guard accessory featured in FIG. 6.
Figure 7B:
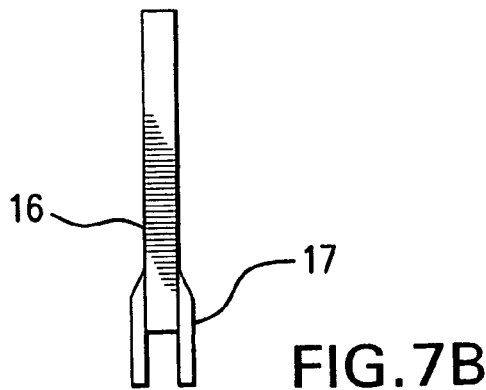
FIG. 7B is a front elevation of the splash guard accessory featured in FIGS. 6 and 7.
Figure 8:
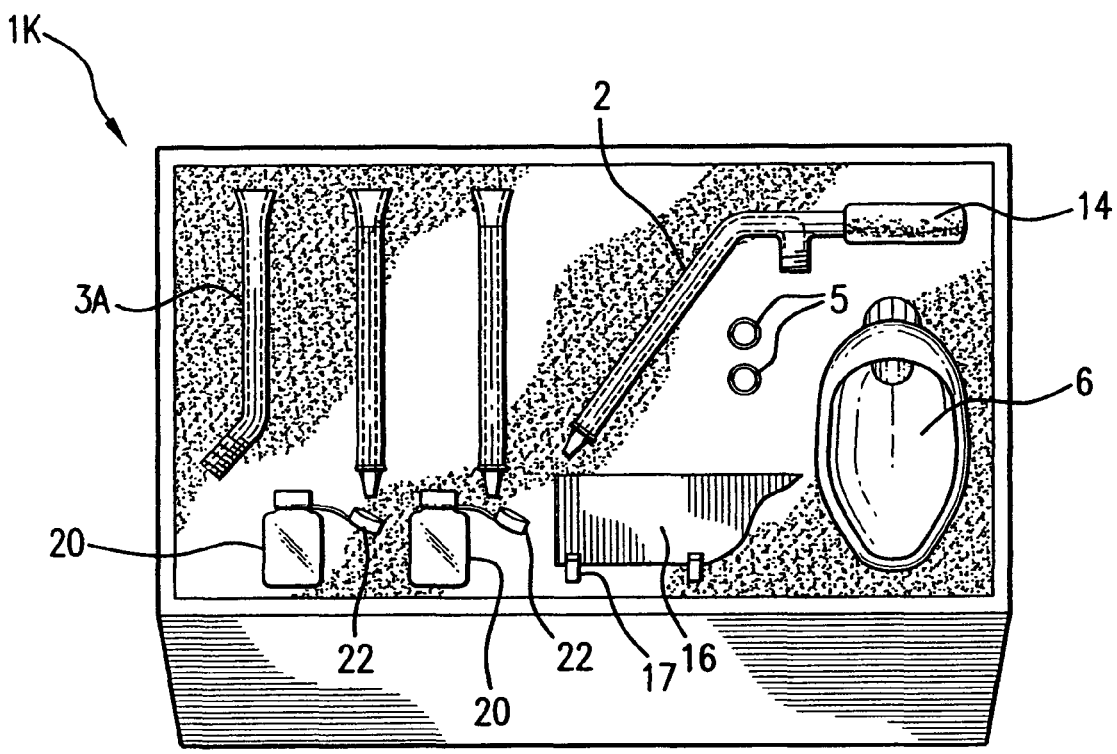
FIG. 8 is a top perspective of a kit featuring disassembled components stored in a container.
Figure 9:
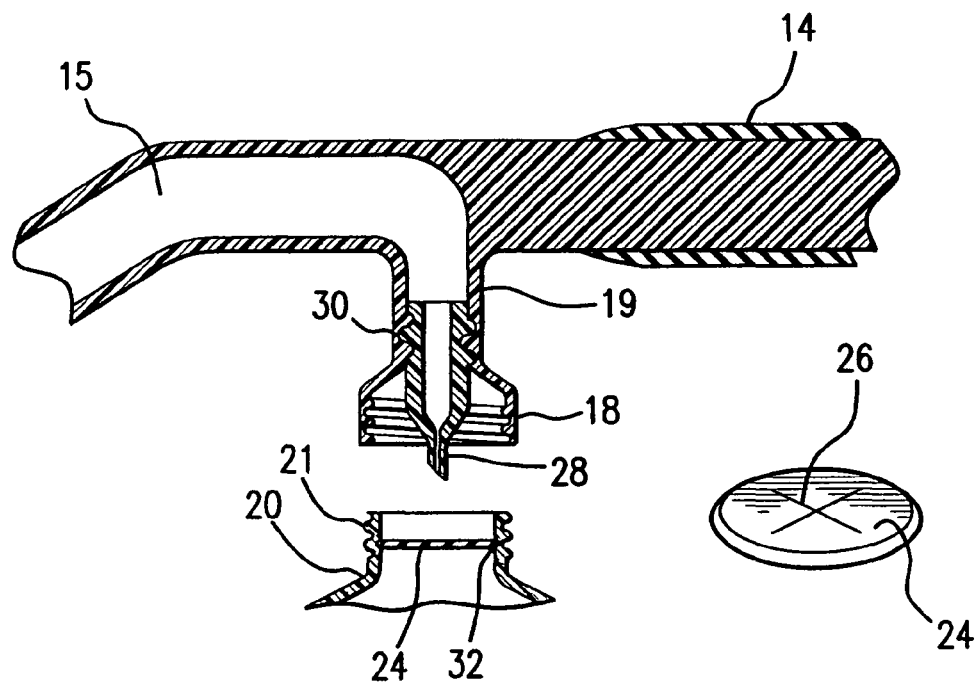
FIG. 9 is a sectional side elevation of a urine sample collection device handle and specimen container collection arrangement.

An optional feature is illustrated in FIGS. 6, 7A and 7B. This is a splash guard panel 16 configured and adapted to be removably mounted on at least one side of tray 6. Mounting clips 17 along a lower edge of splash guard panel 16 fasten by friction-grip, snap-on or other equivalent means to an upper rim of tray 6 when deemed necessary. Male dogs will often discharge urine targeted to a high level where it is difficult to catch with a low profile tray. This splash guard panel feature uniquely offers considerable advantage.

The invention also comprises the method of using the device just described as well as a kit 1K comprising all the components of the invention. Kit 1K includes a convenient storage case which is, as shown, specially configured for conveniently holding components.

Figure 10:
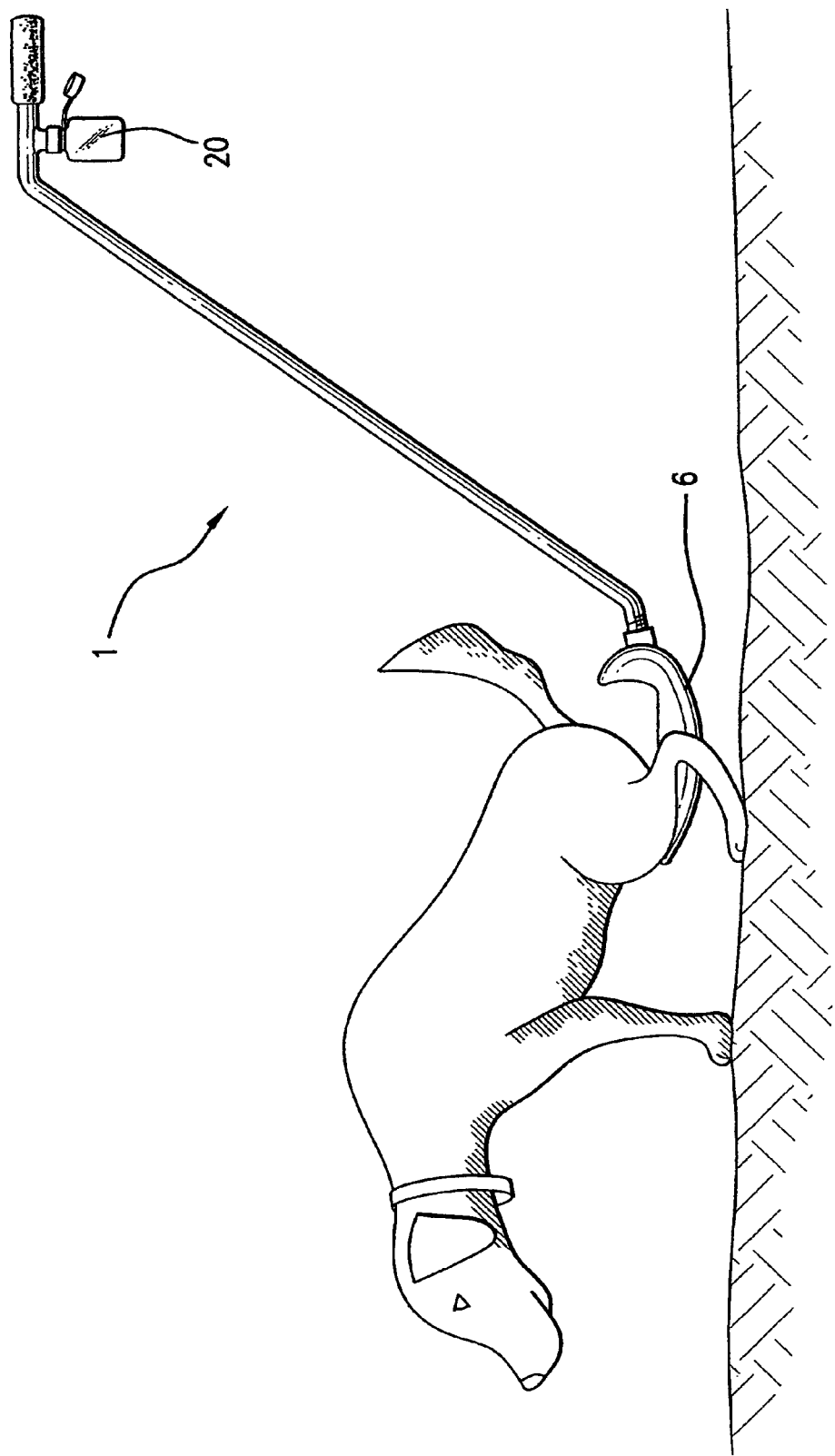
FIG. 10 illustrates a side perspective of the urine sample collection device in use.

The method of collecting pet urine samples is described as follows. The handler provides a kit 1K as described hereabove and assembles the device for application. The handler secures a clean, inert bottle, vial or collection container on container-mount 19. This securing action allows element 28 to pierce flexible wafer 24 at slits 26. As illustrated in FIG. 10, the handler takes the pet, suitably leashed (not shown), for a walk.

Handler may carry device 1, 1A or 1B by hand grip 14 and, as necessary, secondary hand grip 19, 20 (also known as container-mount 19/container 20). The device 1, 1A or 1B is held so that rod handle 2, 3 extends in a generally downwardly slanted angle to position tray 6 immediately behind and below the walking pet. The handler meanwhile is positioned well behind the pet. Rod handle 2, 3 may be manipulated such that one or both hands work to steady tray 6. For example, one hand may hold grip 14 to guide the tray 6 while the second hand holds the pet leash. As necessary, the second hand may be employed to grasp container 20.

When the pet's behavior signals intent to urinate, the handler manipulates tray 6 and gently positions it beneath the pet to catch the urine discharge (not shown). Obviously, tray 6 may at this point be partially supported by the ground or grass immediately beneath the pet. Upon completion of the pet's discharge, or when a sufficient sample is collected, the handler withdraws tray 6 (preferably before the pet's "celebratory scratch" common to just-relieved dogs). Quick withdrawal avoids unwanted collection of grass divots, dirt and mulch which may plug tray 6 outlet at connection 10, or worse, spoil the sample.

Next, the handler lowers hand grip 14 while lifting and tilting tray 6 such that rod handle 2, 3 is at an elevation slightly below tray 6. Given the length of the rod handle 2,3 the required tilting distance is slight causing the captured urine sample to drain from tray 6 into a hollow portion of rod handle 2,3 and to flow further "down" (in its tray 6 tilting position) through rod handle 2,3 to container mount 19 and into container 20. The collected sample flows quickly, without splash-out at funnel 8, through the outlet hole at connection 10, into the hollow rod handle 2, 3 and then on to the collection container 20. Mastering the collection procedure with one hand typically takes little effort. If more steadying effort is required, the container 20 may be grasped and manipulated as a second hand grip.

When the collection container receives the sample, which of course displaces air from the bottle through the membrane wafer 24, the pet owner again tilts the handle rod 2, 3 and returns tray 6 to its previous elevation lower than handle grip 14. At that point in time, or later if more convenient, the pet owner removes container 20 and re-caps it with cap 22 that is temporarily linked to the container by strip 23. The trapped sample typically is stored in a refrigerator until taken to a veterinarian for testing. Handler disassembles device 1, 1A or 1B, washes the components (2, 6, 3A, 3B, 4, 5, 10, 9, 19, 14, 18, 28, and so forth), and returns the clean components to kit K1 for storage.

Although various embodiments of the present invention have been described in the foregoing detailed description an illustrated in the accompanying drawings, it will be understood that the invention is not limited to the embodiments disclosed, but may assume numerous arrangements, rearrangements, modifications, and substitutions of steps without departing from the spirit of the invention nor from the scope of the following claims.

We claim:

1. A device for retrieving urine samples from animals, said device including:
   a collection tray having a first and second end separated by two opposing sides and defining a catch basin therebetween;
   an elongated handle in the form of a rod which is at least partially hollow affixed at its distal end to a connection at said tray second end;
   a container mount configured to interconnect with a sample container, wherein said mount is located at a tap point on said elongated handle and generally above and remote from said tray;
   a sample container removably connected to said container mount;
   said elongated handle terminates in a first hand grip at its proximal end, remote from said distal end;
   said collection tray, handle rod, the container mount and sample container all are in direct flow communication with one another;
   whereby a user in standing position may maneuver said tray beneath a urinating animal by means of said elongated rod to capture a urine sample from said animal, and then said rod and tray may be lifted and tilted to raise said distal end and lower said proximal end permitting the collected sample to flow directly to said container where it is captured.

2. The device for retrieving urine samples from animals as defined in claim 1 wherein;
said tray first and second ends and opposing sides are configured to be generally rounded so as to form a narrow first end compared to a wider second end;
said tray second end includes a hood forming with said basin an outlet funnel;
an outlet from said catch basin is located within said funnel and at a lower portion of said tray.

3. The device for retrieving urine samples from animals as defined in claim 2, and further comprising:
said container mount is located at a predetermined position along said elongated handle and configured to form a second hand grip;
whereby said user can grasp both the first hand grip located at the handle distal end and said second hand grip at a location spaced along said handle so as to steady the user's manipulation of the device to avoid alarming the animal.

4. The device of claim 3 wherein said elongated handle comprises multiple components configured to be interconnected and disassembled;
whereby said device can be assembled with more or fewer components to adjust its overall length, and disassembled for cleaning and storage.

5. The device of claim 1 wherein said container includes an inner element to prevent spillage of captured samples.

6. The device of claim 1 further defined as including:
a flexible membrane wafer is affixed within said container, said wafer including at least one preformed slit that normally is closed;
said container mount includes a generally pointed feeder tube disposed therein and configured so as to extend into said container and pierce said membrane wafer through said at least one slit when said container is fixed to said container mount;
whereby said membrane wafer prevents spillage or backflow of said captured sample while the container is in place on said mount and after its removal therefrom pending, while permitting outflow of air through said slit around said feeder tube when the sample enters.

7. The device of claim 1 further including at least one removable splash guard configured to be mounted on at least one of said opposing sides so as to capture animal urine that is directed above said sides.

8. A kit for retrieving urine samples from animals, said kit including the following elements;
a device with a collection tray having a first and second end separated by two opposing sides and defining a catch basin therebetween;
an elongated handle in the form of a rod which is at least partially hollow and removably affixed at its distal end to a connection to said tray second end;
said handle comprises multiple components configured for interconnection and disassembly;
a container mount on said handle configured to interconnect with a sample container, said mount located generally above and remote from said tray;
a sample container removably connected to said container mount
said elongated handle terminates in a first hand grip at its proximate end, remote from said distal end;
said container mount and said sample container mounted thereon are configured to form a second hand grip;
said collection tray, the at least partially hollow handle rod, the container mount and said sample container are in direct flow communication;
at least one removable splash guard configured to be mounted on at least one of said opposing sides so as to capture animal urine that is directed above said sides;
a storage box configured to secure therein all of the above mentioned elements;
whereby a user may access said kit and assemble the elements therein so as to collect animal urine and store said urine in a collection bottle, and disassemble said elements for washing and return to storage.

9. A method of retrieving urine samples from animals comprising the following steps:
providing a urine collection device including a collection tray with a first and second end separated by two opposing sides and defining a catch basin therebetween;
further providing an elongated handle in the form of a rod which is at least partially hollow affixed at its distal end to a connection at said tray second end and terminating in a first hand grip at its proximal end remote from said distal end;
further providing a container mount configured to interconnect with a sample container, and locating said mount at a tap point on said elongated handle and generally above and remote from said tray;
removably connecting a sample container to said container mount such that said collection tray, handle rod, the container mount and sample container all are in direct flow communication with one another
walking an animal on a leash while following behind said animal with said device;
from a standing position, grasping said first hand grip and manipulating said rod to maneuver said tray beneath the animal;
catching a urine sample discharged from the animal within said tray;
withdrawing said tray and tilting said rod to raise said distal end slightly higher than said proximal end such that said urine sample flows from said tray through said connection and said rod to said tap point and into said sample container;
lowering said distal end and removing said sample container from said mount;
recapping said sample container for testing.

10. The method of claim 9 further including the steps:
configuring said container and mount at said tap point to form a second hand grip;
grasping said device at both said first hand grip and said second hand grip to steady manipulation of the device to avoid alarming the animal.

* * * * *